United States Patent
Elstner

(10) Patent No.: US 6,172,116 B1
(45) Date of Patent: Jan. 9, 2001

(54) USE OF AMINOADAMANTANE COMPOUNDS AS IMMUNOREGULATORS

(75) Inventor: Erich F. Elstner, Gröbenzell (DE)

(73) Assignee: Merz + Co. GmbH & Co., Frankfurt am Main (DE)

(*) Notice: Under 35 U.S.C. 154(b), the term of this patent shall be extended for 0 days.

(21) Appl. No.: 09/029,335

(22) PCT Filed: Aug. 21, 1996

(86) PCT No.: PCT/EP96/03678

§ 371 Date: Jul. 31, 1998

§ 102(e) Date: Jul. 31, 1998

(87) PCT Pub. No.: WO97/07791

PCT Pub. Date: Mar. 6, 1997

(30) Foreign Application Priority Data

Aug. 25, 1995 (DE) .............................. 195 31 342

(51) Int. Cl.[7] .......................... A61K 31/13; C07C 211/03
(52) U.S. Cl. .................. 514/579; 564/461; 564/462
(58) Field of Search ............................ 564/462, 461, 564/1; 514/579

(56) References Cited

FOREIGN PATENT DOCUMENTS 40 14 672 A1  11/1991 (DE) .

OTHER PUBLICATIONS

Immunopharmacology, vol. 6, 1983, pp. 317–325 (M.G. Gil et al).
Int. J. Tiss. React., vol. 7, 1985, pp. 345–350 (S.M. Sanchez et al.).
Immunopharmacology, vol. 18, 1989, pp. 195–204 (C. Clark et al.).
Biochemical Pharmacology, vol. 45, 1993, pp. 1168–1170 (S.G. Evans et al.).
Brit. Journal of Rheumatology, vol. 28, 1989, pp. 521–524 (M H. Pritchared et al.).
Exp. Med. Surg., vol. 23, 1965, pp. 239–242 (E A. Mirand et al.).
Excerpt of The Cell, Chapter 17, pp. 974–982 (1990).

*Primary Examiner*—Joseph McKane
*Assistant Examiner*—Ebenezer Sackey
(74) *Attorney, Agent, or Firm*—Finnegan, Henderson, Farabow, Garrett & Dunner, L.L.P.

(57) ABSTRACT

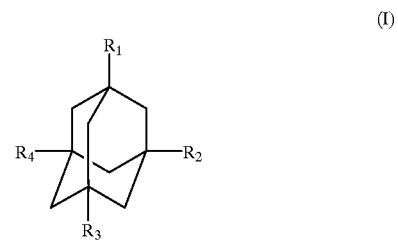

(I)

wherein $R_1$, $R_2$, $R_3$ and $R_4$ are selected independently from each other from —$NR_5R_6$, —$NR_5R_6R_7^+$, hydrogen, aryl or heteroaryl with up to 7 ring members, $C_1$–$C_{20}$-alkyl, $C_1$–$C_{20}$-alkenyl and $C_1$–$C_{20}$-alkinyl, wherein the alkyl, alkenyl and alkinyl residues can be branched, unbranched or cyclized and optionally substituted with halogen, aryl or heteroaryl with up to 7 ring members, with the proviso that at least one of the residues $R_1$, $R_2$, $R_3$ and $R_4$ are represented by —$NR_5R_6$ or —$NR_5R_6R_7$; and $R_5$, $R_6$ and $R_7$ are selected independently from each other from hydrogen, aryl or heteroaryl with up to 7 ring members, $C_1$–$C_{20}$-alkyl, $C_1$–$C_{20}$-alkenyl, $C_1$–$C_{20}$-alkinyl, wherein the alkyl, alkenyl and alkinyl residues can be branched, unbranched or cyclized and optionally substituted with halogen, aryl or heteroaryl with up to 7 ring members, or $R_5$ and $R_6$, together with the nitrogen atom, form a heterocyclic group with up to 7 ring members;

for the regulation of the activity of already activated neutrophils.

10 Claims, 6 Drawing Sheets

Reaction conditions: 10⁶ Neutrophile i.A.; PBS (pH 7,4); 80 μM Luminol; 2,5 mg/ml Zymosan; n = 2x6

Reaction conditions: 10⁶ Neutrophile i.A.; PBS (pH 7,4); 80 μM Luminol; 20 μM A 23187; n = 2x6

Neutrophils stimulated with F-FMLP

Reaction conditions: $10^6$ Neutrophile i.A.; PBS (pH 7,4); 80 μM Luminol; 10 mM N-FMLP; n = 2x6

Neutrophils stimulated with PMA

Reaction conditions: $10^6$ Neutrophile i.A.; PBS (pH 7,4); 80 μM Luminol; 1 μM PMA; n = 2x6

USE OF AMINOADAMANTANE COMPOUNDS AS IMMUNOREGULATORS

The invention relates to the use of aminoadamantane compounds as immunoregulators, especially for the regulation and modulation of already activated neutrophils.

Neutrophils, a subclass of leukocytes, are involved in immune defense and other reactions in the blood vessel system and bordering tissues (Roitt, I. M, Leitfaden der Immunologie, Steinkopf-Verlag Darmstadt, 2nd edition, 1984).

Neutrophils can be activated by exogenous substances, such as for example cell wall components (a commercially obtainable product is "Zymosan"). In connection with this, reactive oxygen species are formed in the so-called respiratory burst.

Figure 1:
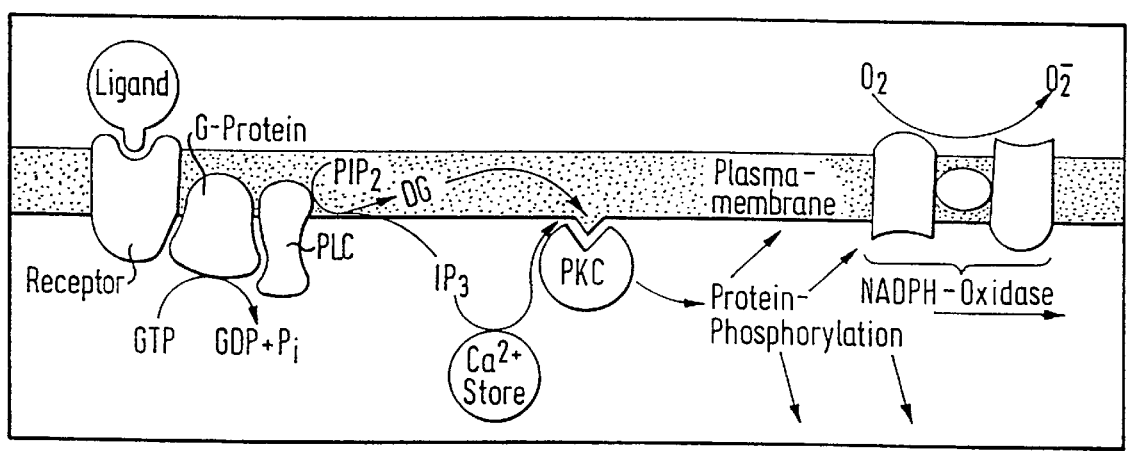

FIG. 1 describes a simplified scheme of neutrophil stimulation: After binding of a ligand (for example, Zymosan A) to a specific receptor on the neutrophil membrane, guanosine triphosphate (GTP) is activated, which in turn activates the phosphatidyl-inositol-4,5-biphosphate (PIP$_2$)-specific phospholipase C (PLC). PLC catalyses the hydrolysis of PIP$_2$ to inositol-1,4,5-triphosphate (IP$_3$) and diacylglycerol (DG). IP$_3$ stimulates the release of Ca$^{2+}$ ions from intracellular stores. Ca$^{2+}$ ions, together with DG, activate the enzyme protein kinase C (PC) which phosphorylates numerous proteins and in this manner activates NADPH oxidase complex among others. NADPH oxidase catalyses in turn the reaction:

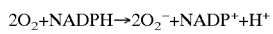

wherein the reactive oxygen species O$_2^-$ results.

Although activated neutrophils are important for a functioning immune defense, disease symptoms such as acute or chronic inflammations or other allergic reactions can result by overreactions caused especially by reactive oxygen species. On the other hand, neutrophil activity can be too low or insufficient for a successful immune defense with a general immune deficiency such as for example with AIDS. Hence, a need exists, especially from the medical standpoint, to be able to influence the regulative and/or modulating activity of neutrophils in vivo and in vitro. In this connection, the neutrophil activity should be either increased or decreased depending on the indication, i.e. should be controllable at will.

Therefore, the object of the present invention is to make available an agent for the regulation and/or modulation of the activity of neutrophils.

It has now been surprisingly found that certain aminoadamantane compounds have a regulative and/or modulating effect on the activity of neutrophils. The present invention relates to this finding. It is decisive for this that the neutrophils have already been activated by other stimulants. The aminoadamantanes themselves do not demonstrate any activating effect on neutrophils.

The above object is accordingly solved by the use of aminoadamantane compounds of formula (I)

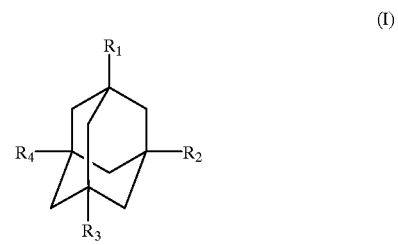

wherein R$_1$, R$_2$, R$_3$ and R$_4$ are selected independently from each other from —NR$_5$R$_6$, —NR$_5$R$_6$R$_7^+$, hydrogen, aryl or heteroaryl with up to 7 ring members, C$_1$–C$_{20}$-alkyl, C$_1$–C$_{20}$-alkenyl and C$_1$–C$_{20}$-alkinyl, wherein the alkyl, alkenyl and alkinyl groups can be branched, unbranched or cyclized and optionally substituted with halogen, aryl or heteroaryl with up to 7 ring members, with the proviso that at least one of the groups R$_1$, R$_2$, R$_3$ and R$_4$ are represented by —NR$_5$R$_6$ or —NR$_5$R$_6$R$_7$; and R$_5$, R$_6$ and R$_7$ are selected independently from each other from hydrogen, aryl or heteroaryl with up to 7 ring members, C$_1$–C$_{20}$-alkyl, C$_1$–C$_{20}$-alkenyl, C$_1$–C$_{20}$-alkinyl, wherein the alkyl, alkenyl and alkinyl groups can be branched, unbranched or cyclized and optionally substituted with halogen, aryl or heteroaryl with up to 7 ring members, or R$_5$ and R$_6$, together with the nitrogen atom, form a heterocyclic group with up to 7 ring members; for the regulation of the activity of already activated neutrophils.

Aminoadamantane compounds of this type are known. Thus, 1-aminoadamantanes are described in DE 22 19 256, DE 28 56 393, DE 22 32 735, U.S. Pat. Nos. 3,450,761 or 4,122,193. The production of compounds of formula (I) generally occurs by known methods, such as for example the alkylation of halogen adamantanes. Subsequent further halogenation and alkylation produce the individual di- and/or tri-substituted adamantanes. EP 392 059, whose teaching is explicitly incorporated herein by reference, is referred to for the production of aminoadamantanes.

Aminoadamantane compounds have also already been used for pharmaceutical purposes. Thus, EP 392 059 discloses the use of 1-aminoadamantane compounds for the treatment of Alzheimer's disease or brain cell damage as a result of cerebral ischemia. U.S. Pat. No. 3,450,761 describes aminoadamantanes with anti-viral activity.

Whether the activity of neutrophils is increased or partially or entirely inhibited depends on the concentration of the aminoadamantane compound used. Thus, concentrations from 10$^{-6}$ to 10$^{-5}$ M have an activity increasing effect. A concentration of about 5·10$^{-6}$ M has proven especially effective for increasing neutrophil activity—a concentration which can be well achieved in vivo in blood plasma. In contrast, an inhibition of activity results with an increase of the aminoadamantane concentration. A concentration suitable for this purpose is 10$^{-4}$ to 10$^{-3}$ M.

The invention comprises adamantane compounds substituted with one or with more amino groups, wherein monoaminoadamantanes are preferred. Hence, suitable compounds of formula (I) are those wherein R$_1$ represents an amino group such as for example 1-amino-3-ethyl-5,7-dimethyl-adamantane; as well as compounds wherein R$_1$ represents an amino group and R$_3$ and R$_4$ represent a hydrogen atom, such as for example 1-amino-3-cyclohexyl-adamantane or 1-amino-3-ethyl-adamantane.

Preferred adamantane compounds are 1-amino-3,5-dimethyl-adamantane, 1-amino-3,5-diethyl-adamantane and the N-substituted compounds 1-N-methylamino-3,5- dimethyl-adamantane and the compound 1-N-ethylamino-3,5-dimethyl-adamantane. Particularly preferred is 1-amino-3,5-dimethyl-adamantane referred to as memantine (INN, Akatinol Memantine®) Görtelmeyer, R., et al, describe the treatment of Demens syndrome with memantine in Spectrum of Neurorehabilitation, W. Zuckschwerdt Publishers, Munich, 1993, 50 ff.

As explained above, the aminoadamantane compounds according to the invention only have a regulating effect on neutrophils which are pre-activated or have been stimulated by special activators.

Natural substances, such as Zymosan, N-formyl-Met-Leu-Phe (N-FLMP) or A 23187 (a Ca antagonist) are known as activators. These substances can be used if one intends to specifically and more intensely activate neutrophils in vitro, but also in vivo. By this, it is possible to detect neutrophils in a sample, f or example in a sample of body fluid, especially a blood sample, even when only few neutrophils are present or when their activity is very weak. In this connection, the activator can be present in combination with the aminoadamantane compound: The degree of activation of the neutrophils stimulated by the activator is intensified by the simultaneous addition of aminoadamantane compound.

A further field of application is the improvement of immune defense in persons with various forms of immune deficiencies, especially AIDS patients. Here, a pharmaceutical composition can be administered which comprises a aminoadamantane compound according to the invention, optionally in combination with a neutrophil activator. Furthermore, the use in CGD (agranulomatosis), Wegener's granulomatosis and/or glycogen storage diseases is possible.

As a matter of course, the neutrophils can also be activated as a consequence of a natural immune response of the organism as a reaction to diverse immunogens and trigger allergic reactions, inflammations and rheumatic symptoms due to overreaction. Here, the neutrophil activity can be attenuated with suitably increased aminoadamantane concentrations and the patient can be given relief. Internal and external inflammation conditions, for example in the knee, hip or jaw and also autoimmune diseases can be particularly combated effectively with aminoadamantane containing medicine. A further field of application is in the treatment of parasitic diseases, such as Leishmannia.

In this connection, it is up to the discretion of the physician to assure the suitable concentration of the aminoadamantane compounds for the regulation and modulation of neutrophil activity by selection of the suitable dose and administration form. Depending on the field of application, parenteral forms, for example intravenous or oral administration forms are possible here; sustained action forms are also suitable. The invention also comprises combinations of the aminoadamantane compounds according to the invention as well as pharmaceutically acceptable salts, especially acid addition salts; for example, hydrochlorides, hydrobromides, sulfates, acetates, succinates, tartrates or addition compounds with fumaric, maleic, citric or phosphoric acid are to be named here. The pharmaceutical compositions can additionally contain a neutrophil activator depending on the range of indications. Customary pharmaceutically acceptable carriers and adjuvants are used for the formulation.

The following example illustrates the dependence of the activity increasing or inhibiting effect of aminoadamantane derivatives by means of the special compound, memantine.

EXAMPLE

Principle of Measurement

The determination of activity of stimulated neutrophils at various memantine concentrations was conducted by chemi-luminescence measurement. Activated neutrophils form reactive oxygen species in the respiratory burst which are detectable as very weak chemiluminescence—so-called low-level or ultra-weak chemiluminescence. To increase the photon yield, luminol is added as a sensitizer (indicator dependent chemiluminescence). Luminol is a cyclic hydrazide which can be oxidized to diazoquinone through reactive oxygen species. By a nucleophil attack of a hydrogen peroxide anion, this diazoquinone is further converted to a-hydroxyhydroperoxide which disintegrates into aminophtalate under light emission. Reaction batch:

| | |
|---|---|
| Neutrophils: | $10^6$ i.A. |
| PBS-buffer pH (7.4): | to 250 ml |
| luminol: | 80 mM |
| memantine: | var. conc. |
| stimulation agent: | |
| Zymosan | 2.5 mg/ml |
| or PMA | 1 mM |
| or A 23187 | 20 mM |
| or N-FLMP | 10 mM |

PBS = Phosphate Buffered Saline

Analogous reaction batches can be produced with further adamantane compounds.

Measurement

Measurement was conducted with very sensitive, low-noise photomultipliers which convert photons on a photocathode into primary electrons and then multiply amplify these to an electrical impulse signal.

The reaction is started with a stimulation agent and measured without incubation time for 40 min (=80 cycles).

Results

Figure 2:
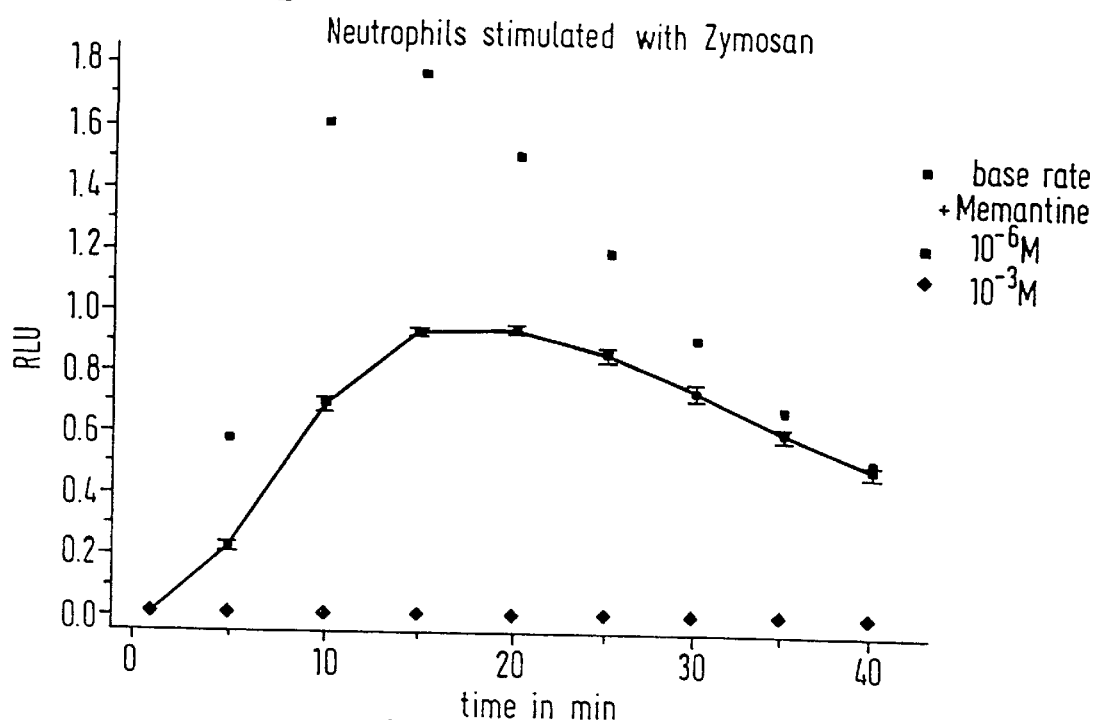
Figure 3:
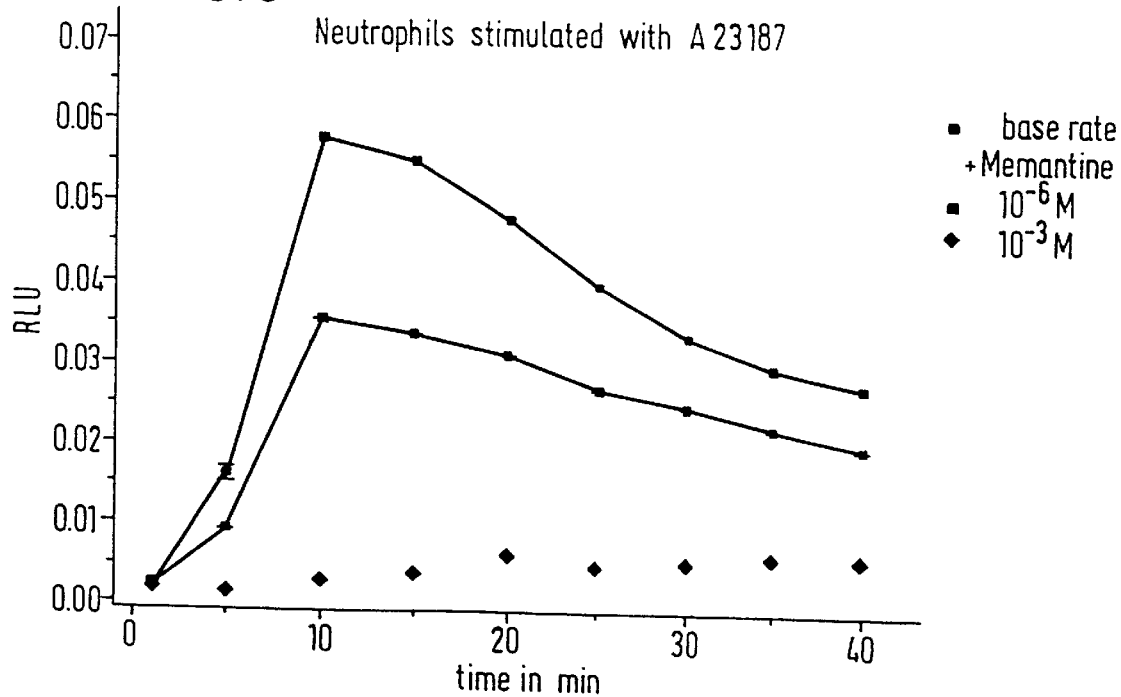
Figure 4:
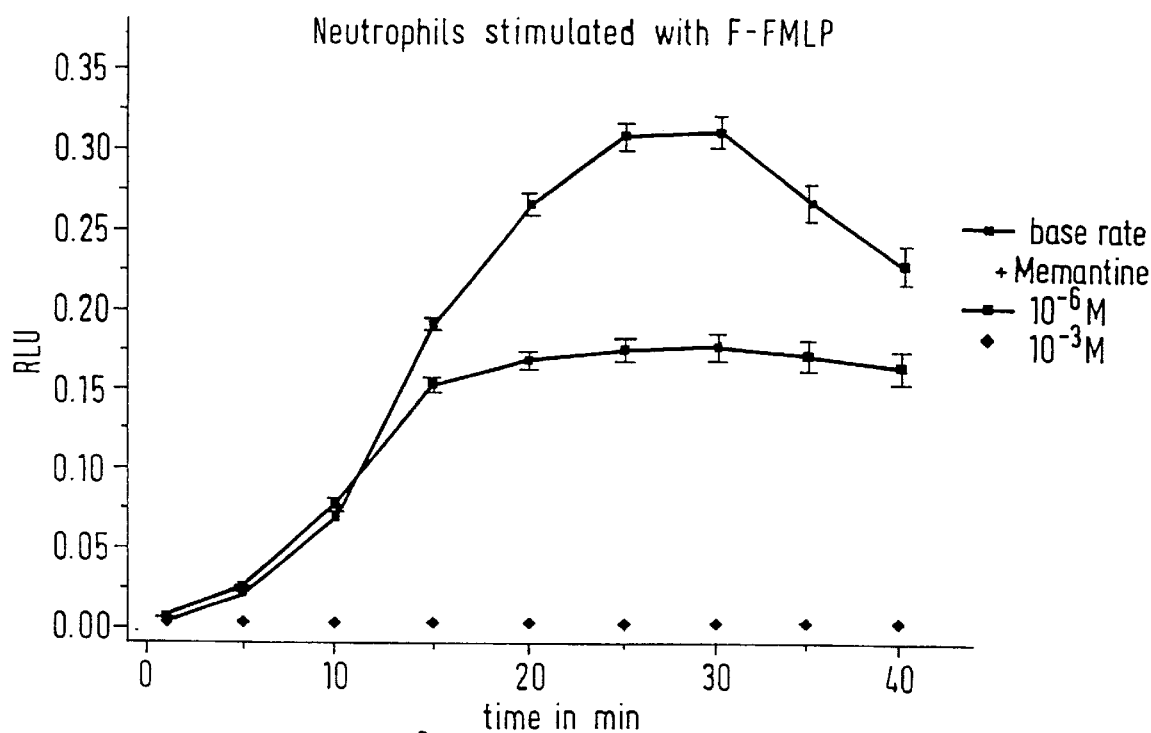
Figure 5:
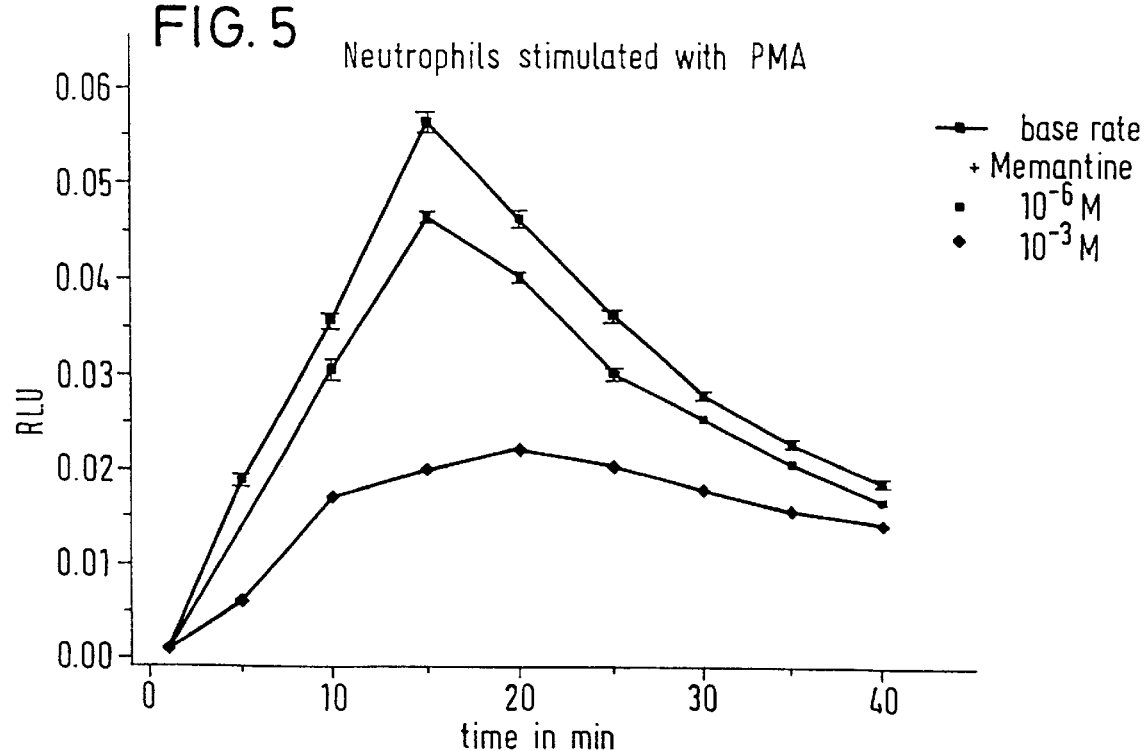

With neutrophils which were activated with natural stimulation agents (Zymosan A; a23187; N-formyl-Met-Leu-Phe), the RLU-base rate (RLU =Relative Light Units) can be additionally increased with $10^{-6}$ M memantine (Zymosan A by about 90%; A 23187 by about 60%; N-FMLP by about 78% of the base stimulation) [FIG. 2–4]. This suggests an increased respiratory burst and an increased phagocytosis activity. This reaction does not occur by stimulating with toxic Phorbol-Mystrate-Acetate (about −20% of the base stimulation) [FIG. 5]. In contrast, memantine almost completely inhibits the base stimulation of all stimulating agents at a concentration of $10^{-3}$.

In a control experiment, it can be shown that memantine itself has neither chemiluminescence nor quenches chemi-luminescence (not shown).

Specificity of the Activation Regulation

Figure 6:
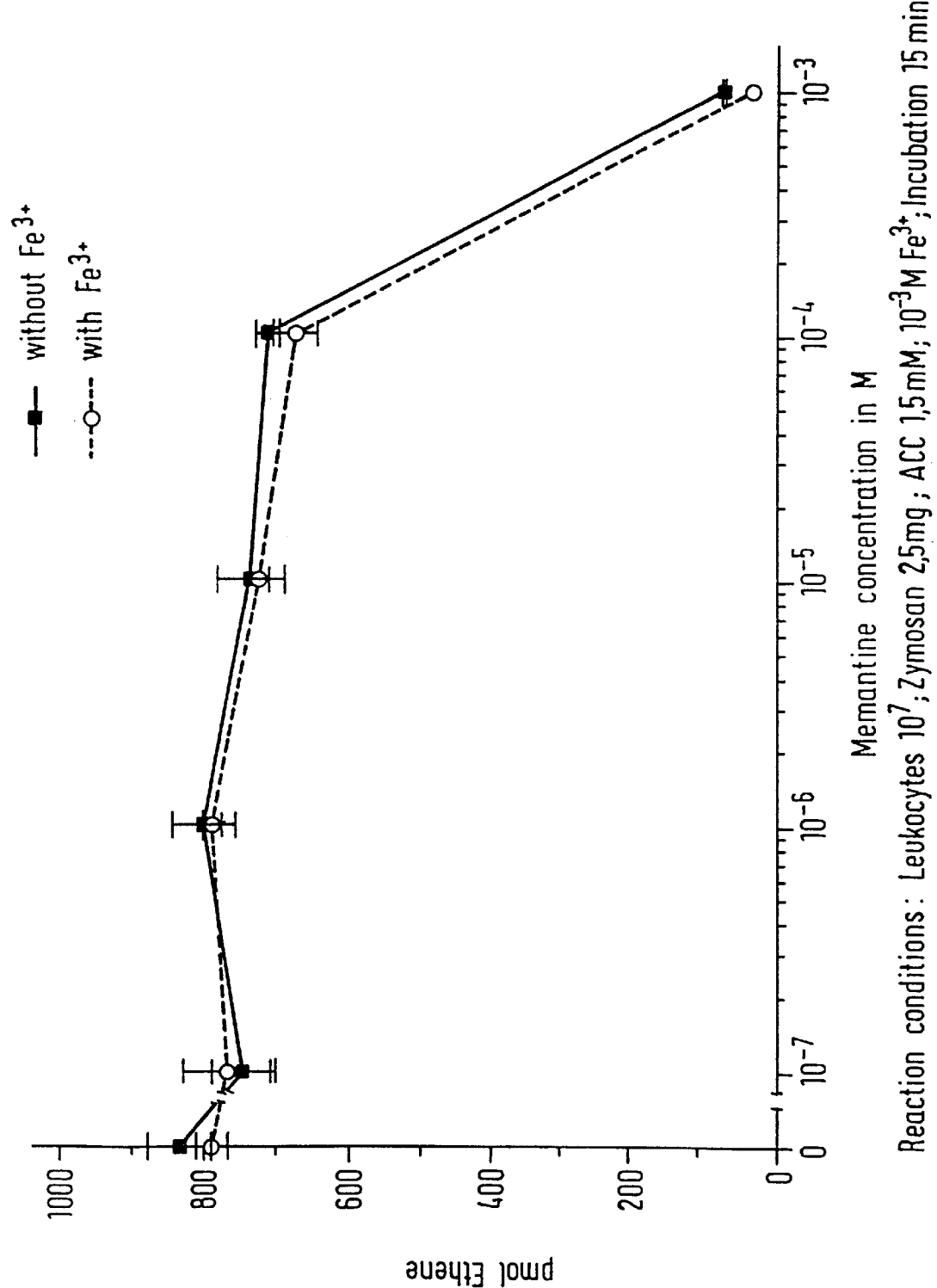

The regulative effect of the aminoadamantane compounds according to the invention is highly specific for neutrophils. Thus, the aminoadamantane compounds do not show any action on the deregulation effect of activated leukocytes. It emerges from FIG. 6 that ACC (1-aminocyclopropane-1-carboxylic acid) itself does not react with memantine in relatively high concentrations. ACC is a specific indicator for myeloperoxidase which is released by degranulation of leukocytes and forms damaging hypochlorite in extracellular spaces. Myeloperoxidase reacts specifically with ACC under formation of ethylene which can be detected gaschromatographically. Therewith, the formed amount of ethylene represents an indirect measuring quantity for leukocyte activity.

Figure 7:
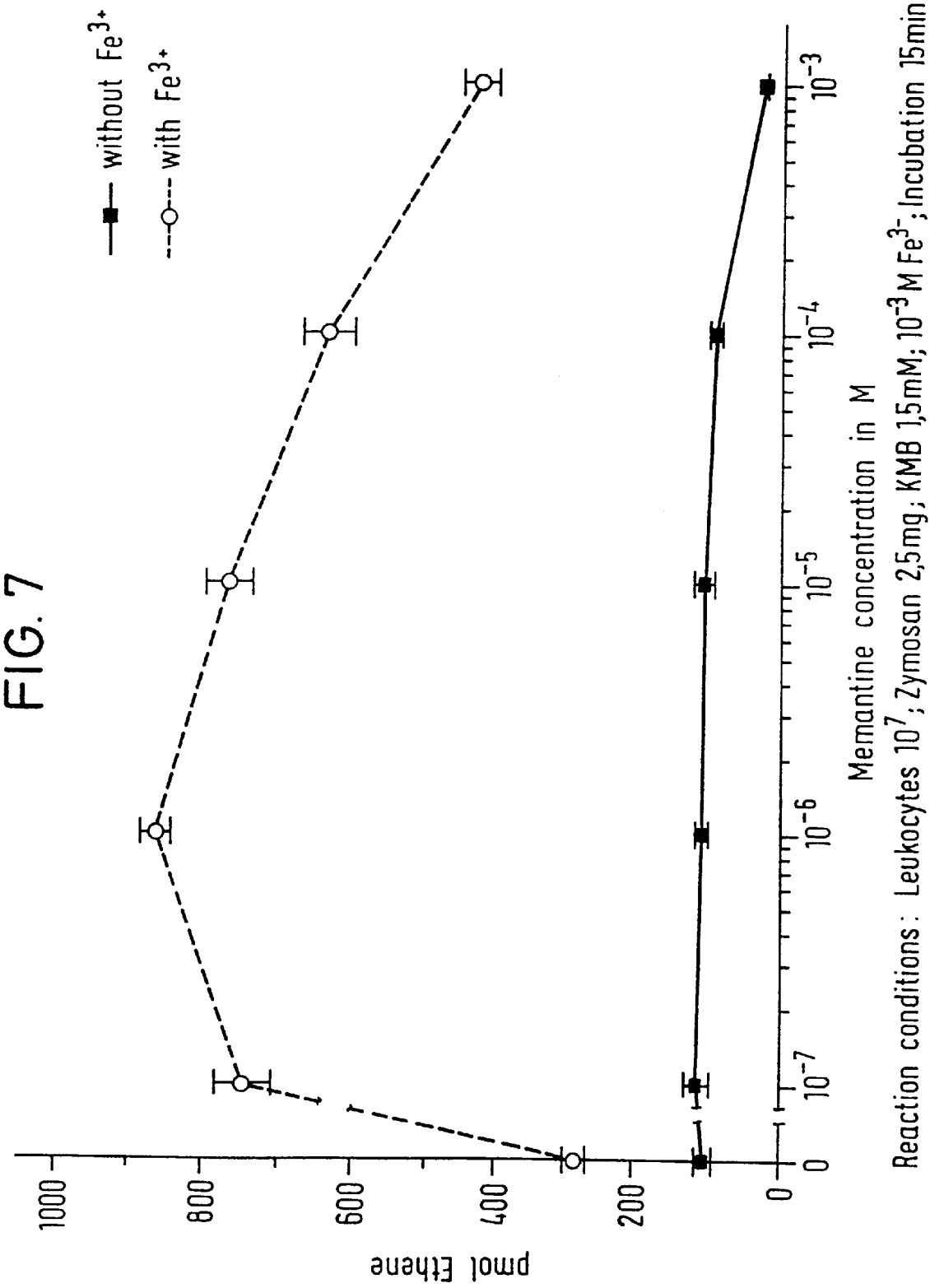

In contrast, the indicator for the respiratory burst and the oxygen radicals arising therefrom (superoxide, OH-radicals and hydrogenperoxide) are activated by memantine. This is already shown at a concentration of only $10^{-7}$ M which can easily be obtained in vivo. The activation effect can be made visible by addition of $Fe^{3+}$ which shifts the equilibrium of the reaction through the Haber-Weiβ reaction from superoxide and hydrogenperoxide to the direction of OH radicals. A sensitive indicator for oxygen species of this type is KMB (a-keto-g-methylthiobutyrate) which disintegrates into ethylene, among others, under oxidative conditions and which can be easily detected [FIG. 7].

Figure 8:
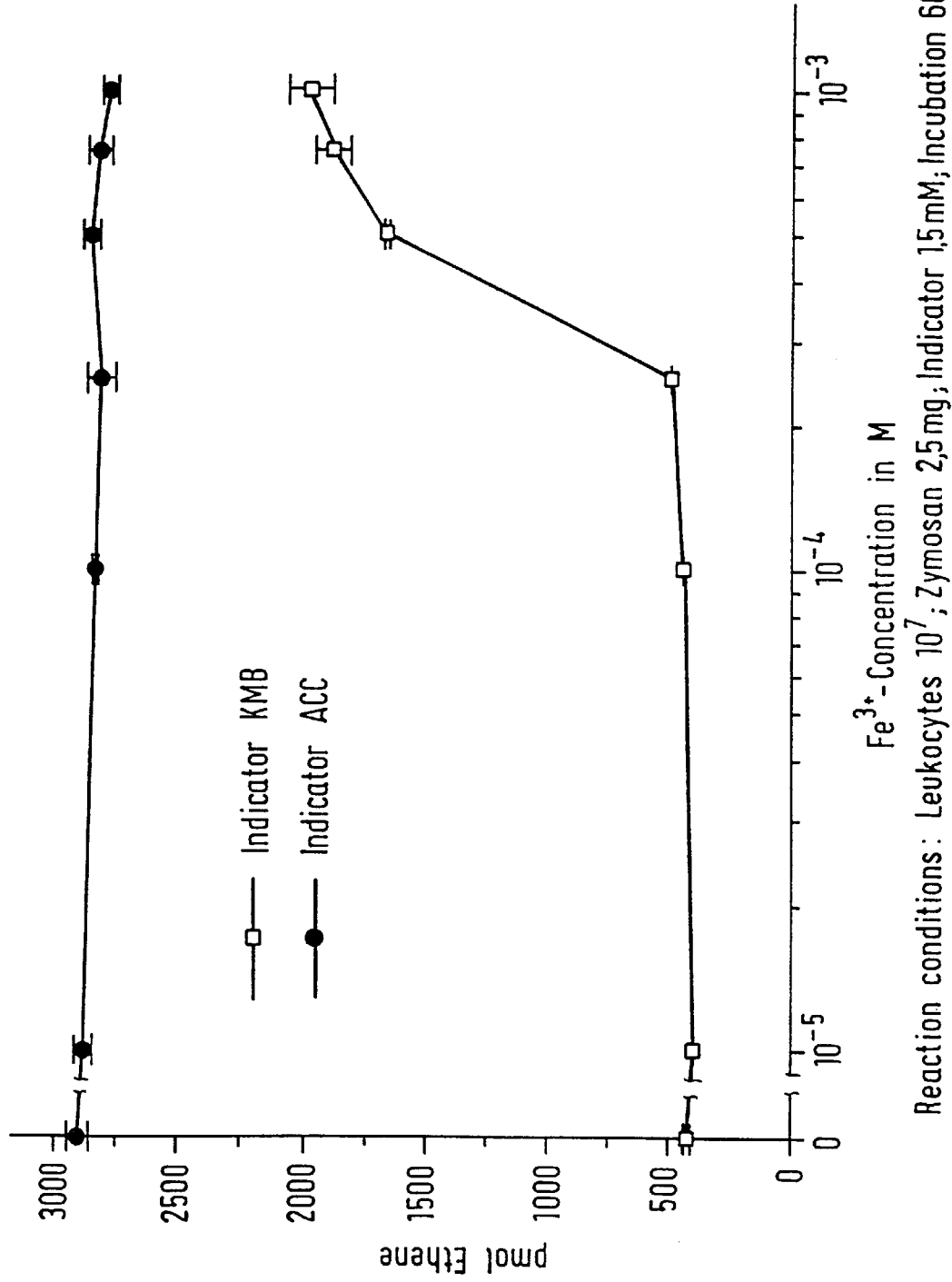

As a control, FIG. 8 shows that the KMB-reaction, but not the ACC-reaction, is stimulated first by the addition of $Fe^{3+}$ at the concentration of $>5\times10^{-4}$ M. $Fe^{3+}$ alone is without influence.

What is claimed is:

1. A process for increasing the activity of already activated neutrophils which comprises contacting said neutrophils with an aminoadamantane compound of formula (I)

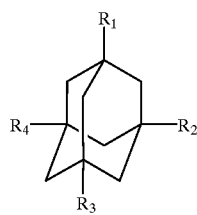

(I)

wherein $R_1$, $R_2$, $R_3$ and $R_4$ are selected independently from each other from —$NR_5R_6$, —$NR_5R_6R_7^+$, hydrogen, aryl or heteroaryl with up to 7 ring members, $C_1$–$C_{20}$-alkyl, $C_1$–$C_{20}$-alkenyl and $C_1$–$C_{20}$-alkynyl, wherein the alkyl, alkenyl and alkynyl groups can be branched, unbranched or cyclized and optionally substituted with halogen, aryl or heteroaryl with up to 7 ring members with the proviso that at least one of the groups $R_1$, $R_2$, $R_3$ and $R_4$ are represented by —$NR_5R_6$ or —$NR_5R_6R_7^+$; and $R_5$, $R_6$ and $R_7$ are selected independently from each other from hydrogen, aryl or heteroaryl with up to 7 ring members, $C_1$–$C_{20}$-alkyl, $C_1$–$C_{20}$-alkenyl, $C_1$–$C_2$ -alkynyl, wherein the alkyl, alkenyl and alkynyl groups can be branched, unbranched or cyclized and optionally substituted with halogen, aryl or heteroaryl with up to 7 ring members, or $R_5$ and $R_6$, together with the nitrogen atom, form a heterocyclic group with up to 7 ring members in a concentration of said aminoadamantane compound of from $10^{-6}$ to $10^{-5}$M.

2. The process of claim 1, wherein the aminoadamantane compound of formula (I) is selected from the group consisting of 1-amino-3-ethyl-5,7-dimethyl-adamantane,
1-amino-3-cyclohexyl-adamantane,
1-amino-3-ethyl-adamantane,
1-amino-3,5-dimethyl-adamantane,
1-amino-3,5-diethyl-adamantane,
1-N-methylamino-3,5-dimethyl-adamantane, and
1-N-ethylamino-3,5-dimethyl-adamantane.

3. The process of claim 1 or 2, wherein the activity of the neutrophils is increased in vitro.

4. The process of claim 1 or 2, for the treatment of CGD (agranulomatosis), Wegener's granulomatosis and/or immune deficiency diseases.

5. A medicament for increasing the activity of neutrophils comprising an aminoadamantane compound of formula (I);

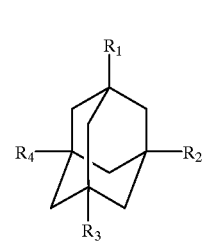

(I)

wherein $R_1$, $R_2$, $R_3$ and $R_4$ are selected independently from each other from —$NR_5R_6$, —$NR_5R_6R_7^+$, hydrogen, aryl or heteroaryl with up to 7 ring members, $C_1$–$C_{20}$-alkyl, $C_1$–$C_{20}$-alkenyl and $C_1$–$C_{20}$-alkynyl, wherein the alkyl, alkenyl and alkynyl groups can be branched, unbranched or cyclized and optionally substituted with halogen, aryl or heteroaryl with up to 7 ring members with the proviso that at least one of the groups $R_1$, $R_2$, $R_3$ and $R_4$ are represented by —$NR_5R_6$ or —$NR_5R_6R_7^+$; and $R_5$, $R_6$ and $R_7$ are selected independently from each other from hydrogen, aryl or heteroaryl with up to 7 ring members, $C_1$–$C_{20}$-alkyl, $C_1$–$C_{20}$-alkenyl, $C_1$–$C_{20}$-alkynyl, wherein the alkyl, alkenyl and alkynyl groups can be branched, unbranched or cyclized and optionally substituted with halogen, aryl or heteroaryl with up to 7 ring members, or $R_5$ and $R_6$, together with the nitrogen atom, form a heterocyclic group with up to 7 ring members in a concentration of from $10^{-6}$ to $10^{-5}$M and an activator for neutrophils.

6. A process for amplified, specific activation of already activated neutrophils in vivo or in vitro which comprises contacting said neutrophils with a composition comprising an aminoadamantane compound formula (I)

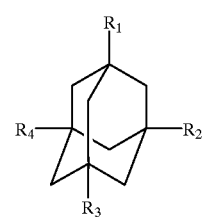

(I)

wherein $R_1$, $R_2$, $R_3$ and $R_4$ are selected independently from each other from —$NR_5R_6$, —$NR_5R_6R_7^+$, hydrogen, aryl or heteroaryl with up to 7 ring members, $C_1$–$C_{20}$-alkyl, $C_1$–$C_{20}$-alkenyl and $C_1$–$C_{20}$-alkynyl, wherein the alkyl, alkenyl and alkynyl groups can be branched, unbranched or cyclized and optionally substituted with halogen, aryl or heteroryl with up to 7 ring members with the proviso that at least one of the groups $R_1$, $R_2$, $R_3$ and $R_4$ are represented by —$NR_5R_6$ or —$NR_5R_6R_7^+$; and $R_5$, $R_6$ and $R_7$ are selected independently from each other from hydrogen, aryl or heteroaryl with up to 7 ring members, $C_1$–$C_{20}$-alkyl, $C_1$–$C_{20}$-alkenyl, $C_1$–$C_{20}$-alkynyl, wherein the alkyl, alkenyl and alkynyl groups can be branched, unbranched or cyclized and optionally substituted with halogen, aryl or heteroaryl with up to 7 ring members, or $R_5$ and $R_6$, together with the nitrogen atom, form a heterocyclic group with up to 7 ring members in a concentration of from $10^{-6}$ to $10^{-5}$ M; and an activator for the neutrophils.

7. The process of claim 6, wherein the neutrophils are detected in a sample.

8. The process of claim 6 or 7, wherein the activator is selected from the groups consisting of Zymosan, N-formyl-Met-Leu-Phe and A 23187.

9. The medicament of claim 5, wherein the aminoadamantane compound of formula (I) is selected from the group consisting of 1-amino-3-ethyl-5,7-dimethyl-adamantane, 1-amino-3-cyclohexyl-adamantane, 1-amino-3-ethyl-adamantane, 1-amino-3,5-dimethyl-adamantane, 1-amino-3,5-diethyl-adamantane, 1-N-methylamino-3,5-dimethyl-adamantane, and 1-N-ethylamino-3,5-dimethyl-adamantane.

10. The medicament of claim 5, wherein the activator is selected from the group consisting of Zymosan, N-formyl-Met-Leu-Phe and A 23187.

* * * * *